United States Patent [19]
Dyer et al.

[11] Patent Number: 4,652,587
[45] Date of Patent: Mar. 24, 1987

[54] F-T PROCESS USING AN IRON ON MIXED ZIRCONIA-TITANIA SUPPORTED CATALYST

[75] Inventors: Paul N. Dyer, Allentown; Andrew F. Nordquist, Whitehall; Ronald Pierantozzi, Macungie, all of Pa.

[73] Assignee: Air Products and Chemicals, Inc., Allentown, Pa.

[21] Appl. No.: 875,803

[22] Filed: Jun. 18, 1986

Related U.S. Application Data

[62] Division of Ser. No. 752,203, Jul. 3, 1985.

[51] Int. Cl.$^4$ .............................................. C07C 1/04
[52] U.S. Cl. .................................... 518/717; 518/721
[58] Field of Search ........................ 518/717, 719, 721

[56] References Cited

U.S. PATENT DOCUMENTS 4,548,953 10/1985 Fiato et al. ........................ 518/721

Primary Examiner—Howard T. Mars
Attorney, Agent, or Firm—Willard Jones, II; James C. Simmons; E. Eugene Innis

[57] ABSTRACT

A Fischer-Tropsch catalyst comprising iron co-deposited with or deposited on particles comprising a mixture of zirconia and titania, preferably formed by co-precipitation of compounds convertible to zirconia and titania, such as zirconium and titanium alkoxide. The invention also comprises the method of making this catalyst and an improved Fischer-Tropsch reaction process in which the catalyst is utilized.

6 Claims, No Drawings

F-T PROCESS USING AN IRON ON MIXED ZIRCONIA-TITANIA SUPPORTED CATALYST

This invention was made under DOE contract No. DE-AC22-80PC30021 (DOE) and is subject to government rights arising therefrom.

This is a division of application Ser. No. 752,203, filed July 3, 1985.

FIELD OF THE INVENTION

This invention pertains to a catalytic composition and a method of making that composition, as well as the use of that composition in the selective hydrogenation of carbon monoxide in a Fischer-Tropsch process such as the selective catalytic conversion of synthesis gas to liquid hydrocarbons.

Liquid hydrocarbon fuels or chemicals can be produced from coal by indirect liquefaction. This involves the production of synthesis gas by coal gasification. The synthesis gas is then further converted to fuels or chemicals by hydrogenation of the carbon monoxide in the synthesis gas, typically in a Fischer-Tropsch ("F-T") synthesis. New generation coal gasifiers, such as those produced by Westinghouse, Texaco or Shell-Kopper's partial oxidation processes, produce a $CO/H_2$ mixture that is CO rich (1:1 to 2:1 $CO/H_2$). To maximize the efficiency of the overall process of indirect liquefaction, a need exists for Fischer-Tropsch catalysts capable of synthesizing hydrocarbons and/or chemicals directly with CO rich synthesis gas, preferably selectively converting the carbon monoxide to hydrocarbons having from 5 to 25 carbons, referred to herein as $C_5$-$C_{25}$ hydrocarbons, sometimes referred to as liquid hydrocarbons.

While the Fischer-Tropsch synthesis has been studied extensively, most previous research has involved fixed bed, gas/solid reactors. Early work was reviewed by Storch, Columbic and Anderson (H. H. Storch, N. Columbic, R. B. Anderson, "The Fishcher-Tropsch and Related Syntheses", Wiley 1951). Slurry phase F-T synthesis carried out more recently has been reviewed by Kolbel and Ralek (H. Kolbel, M. Ralek, *Catal. Rev. Sci. Eng.*, 1980, 21, 225) and Poutsma (M. L. Poutsma, ORNL5635, 1980, "Assembly of Advanced Process Concepts for the Liquefaction of Low $H_2$/CO Ratio Synthesis Gas"), where the potential incentives for using high $CO/H_2$ ratio syngas in liquid phase slurry reactors were pointed out. Satterfield, et al. recently examined literature on product distributions in F-T synthesis, using Fe catalysts (C. N. Satterfield, G. A. Huff, J. P. Longwell, *Ind. Eng. Chem. Proc. Des. Dev.*, 1982, 21, 465).

While the known prior art shows various combinations of catalytic materials, some of which include one or more of the elements iron, titanium and zirconium, none includes the specific combination as disclosed and claimed herein; nor does the prior art disclose a method of making or using a catalytic composition similar to or suggestive of that disclosed and claimed herein.

SUMMARY OF THE INVENTION

The present invention comprises a porous, catalytically active composition comprised of a mixture of zirconium dioxide and titanium dioxide, combined with iron or iron oxide, either as a surface impregnant on the particles or as an interdispersion with the zirconium dioxide and titanium dioxide.

Preferably, the zirconium dioxide/titanium dioxide mixture is produced by co-precipitation of precursor materials convertible by drying and calcining in air or other oxygen-containing atmosphere to zirconium dioxide and titanium dioxide. Similarly, either iron or iron oxide is preferably incorporated with the zirconium dioxide/titanium dioxide combination by impregnation or co-precipitation of an iron precursor; conversion of the iron precursor to iron oxide is accomplished by drying and calcining in air or other oxygen-containing atmosphere; and, in the case of a catalytically active composition with elemental iron, further conversion of the iron oxide to iron by reducing in a reducing atmosphere.

Still other catalytic compounds such as an alkali metal compound, e.g. potassium bicarbonate, may also be included in a concentration of up to 10%, by weight. The additional compound may be incorporated in the catalyst by impregnation or deposition on the particulate material.

The iron content of this catalytic composition may be from 0.1 to 90%, by weight, preferably 5–15%, by weight. The zirconium:titanium atomic ratio generally is in the range 2:1 to 1:2 preferably about 1:1.

This invention further encompasses the process wherein the catalytic composition described above, made as described, is activated (gradually subjected to elevated temperature and pressure over a period of time and in a reducing atmosphere) and then contacted with carbon monoxide in the presence of hydrogen (e.g. synthesis gas with a relatively high $CO:H_2$ molar ratio—from 1:1 to 2:1) at elevated temperature and pressure, hereby the carbon monoxide is selectively converted to liquid hydrocarbons.

For a better understanding of this invention, reference may be made to the detailed description thereof which follows, taken together with the subjoined claim.

DETAILED DESCRIPTION OF THE INVENTION

The various forms of catalytic composition within the scope of the present invention may best be described by reference to the method of making these catalytic compositions in accordance with the present invention. In all cases, the essential catalytic ingredients in this invention, namely an intimate mixture of zirconium dioxide and titanium dioxide further combined with iron or iron oxide, are produced by co-precipitation or deposition of a precursor material which convert to the desired oxide upon drying and calcining in an oxygen-containing atmosphere, such as air (typically drying at 90°–110° C. and calcining at 500°–550° C. each for times sufficient to effect drying or calcining, typically in the range 1–20 hours) and to elemental metal upon reducing in a reducing atmosphere for sufficient time to convert the metal oxide to the metal. The zirconium dioxide and titanium dioxide precursors typically comprise zirconium and titanium alkoxides, the alkoxides comprising 1 to 5 alkyl carbon atoms. Such alkoxides may be deposited from a solution with a non-reactive solvent therefor, such as propanol or some other alcohol, by the addition of water or a hydroxyl compound, typically ammonium hydroxide. The process may be referred to as hydrolyzing the alkoxide solution and may consist simply of adding water to the solution.

Iron precursor compounds include iron oxide, hydrated iron oxide, iron hydroxide, iron acetate, iron benzoate, iron oxalate, iron maleate, iron nitrate, iron sulfate, iron gluconate, iron citrate, and iron lactate. By definition, iron compounds include both the ferric and ferrous forms and mixtures thereof. Such compounds may be dry blended with the Zr/Ti dioxide particles or deposited from solution by raising the pH of the solution. All convert, upon application of heat, such as by drying and calcining, to iron oxide, which in turn may be reduced to iron in the process of activating the catalyst for the F-T reaction.

The co-precipitate formed in accordance with this invention typically is catalytically active, in part because of its high surface area. This may be enhanced by grinding the precipitate. The surface area of the catalytic material is generally at least 100 square meters per gram, preferably 200 square meters per gram for optimum catalytic effectiveness.

The preferred titanium and zirconium alkoxide precursor materials are the butoxides and propoxides of these metals.

The catalytic effectiveness of these materials may also be enhanced by further combination with other catalytic materials, such as co-precipitated cobalt or nickel compound. Preferably, it is impregnated with an alkali metal compound by deposition of a compound such as potassium bicarbonate or potassium carbonate.

The catalytic material of this invention is preferably used in the Fischer-Tropsch selective hydrogenation of carbon monoxide in high $CO:H_2$ ratio synthesis gas to produce liquid hydrocarbons. For this purpose, the catalytic material is first activated, in a conventional manner, by gradually exposing it to increasing pressures and temperatures up to on the order of 550° C. and 300 psig in a reducing atmosphere, such as a hydrogen containing atmosphere or the synthesis gas itself. The activated catalyst is then exposed to the carbon monoxide-hydrogen reactive mixture, typically synthesis gas, in a tubular fixed bed reactor or in a slurry phase reactor.

In the preferred form of the catalytic material of the present invention, in which the iron is coprecipitated with the zirconium dioxide and titanium dioxide compounds, the iron may produce a more favorable particle size distribution than in the iron impregnated forms of the present invention. The coprecipitated catalyst has higher specific activity than does the impregnated iron-zirconium dioxide-titanium dioxide support.

This invention has been the subject of numerous experimental syntheses and demonstrations, examples of which are set forth below. Those examples referred to as "comparative" are included only for purposes of comparing the invention to typical prior art catalysts and processes outside the scope of the present invention.

Examples 1-2 pertain to the making of an impregnated zirconia/titania support catalyst in accordance with the present invention. Analyses of these catalysts are summarized in Table 1.

EXAMPLE 1

$ZrO_2.TiO_2$ was prepared by co-precipitation of equimolar mixtures of $Zr(OC_3H_7)_4$ and $Ti(OC_3H_7)_4$ in propanol with water. 50 g $Ti(OC_3H_7)_4$ and 57.5 g of $Zr(OC_3H_7)_4$ were dissolved in 200 ml of dry degassed 1-propanol at room temperature. To this was added, with stirring, 200 ml of 50% isopropanol in water to precipitate the hydroxides. The resultant precipitate was washed with water, dried at 110° C. in air, and calcined at 550° C. in air for 2 hours to produce $ZrO_2$ and $TiO_2$, intimately mixed in a particulate material with a surface area of 200 $m^2$/gram.

Iron was added by impregnation of the support with an aqueous solution of $Fe(NO_3)_3$. 25.5 g of calcined $ZrO_2.TiO_2$ was impregnated with 32.54 g of $Fe(NO_3)_3.9H_2O$ dissolved in 30 ml of water. To this solution was added ammonium hydroxide to precipitate iron nitrate. The product was dried in air at 110° C. for 16 hours, and then calcined at 510° C. in air for 2 hours to convert the iron nitrate to $Fe_2O_3$.

EXAMPLE 2

Ferrous oxalate was supported on another sample of the mixed $ZrO_2.TiO_2$ precipitate described above before $Fe(NO_3)_3$ addition). Specifically 14.49 g of $Fe(C_2O_4).2H_2O$ was dry blended with 22.5 g of $ZrO_2.TiO_2$. This material was then calcined in air at 550° C. for 2.5 hours, to convert the iron oxalate to iron oxide, and then "promoted" with 0.2% potassium by addition of $K_2CO_3$ in $H_2O$ to incipient wetness followed by drying at 110° C. for 2 hours.

The following examples (3–6) illustrate the preparation of co-precipitated $Fe_2O_3.ZrO_2$ $TiO_2$ catalysts. The analyses of these catalysts are summarized in Table 2.

EXAMPLE 3

$Fe(CH_3COO)_2$ (ferrous acetate) was hydrated by exposing it to water saturated air for 3 days at 20° C. Fifty-six grams of hydrated $Fe(CH_3COO)_2$, 91.4 g of $Ti(OC_3H_7)_4$ and 105.4 g of $Zr(OC_3H_7)_4$ were dissolved in 1300 ml of dry 1-propanol. To this solution was added with stirring a solution containing 47.0 ml $H_2O$, 100 ml 1-propanol, and 20 g of 28.9% aqueous $NH_3$. The resulting precipitate was washed with water and dried in air for 16 hours at 110° C. to produce a co-precipitated mixture of iron oxide and zirconium and titanium dioxides in particle form. This catalyst was promoted with 0.29% K by incipient wetness addition of $K_2CO_3$ and again dried in air at 110° C. for 5 hours.

EXAMPLE 4

Another sample of the co-precipitated iron oxide, titanium dioxide, zirconium dioxide mixture described above in Example 3 was promoted with 8.0% K by incipient wetness addition of $K_2CO_3$ and dried in air at 110° C. for 5 hours. It was then calcined in air at 550° C. for 2 hours.

EXAMPLE 5

Twenty-eight grams of drated iron acetate, 91.4 g of $Ti(OC_3H_7)_4$ and 105.4 g of $Zr(OC_3H_7)_4$ were dissolved in 1300 ml of dry 1-propanol. To this solution was added, with stirring, a solution containing 47.0 ml $H_2O$, 100 ml 1-propanol and 20 g of 28.9% aqueous $NH_3$. The resulting precipitate was washed with water and dried in air for 16 hours at 110° C.

This catalyst was promoted with 0.2% K by incipient wetness addition of $K_2CO_3$. After air drying at 110° C. for 16 hours, the catalyst was calcined at 500° C. for 2 hours.

EXAMPLE 6

A separate sample of the above-described catalyst (Example 5) was promoted with 9.4% K, dried and calcined as in Example 5.

The following examples illustrate the utility of the $Fe/ZrO_2.TiO_2$ catalyst of this invention for the production of diesel range hydrocarbons. Results are shown in Tables 3 and 4.

EXAMPLE 7

The calcined, iron nitrate impregnated catalyst of Example 1 was activated and used for CO hydrogenation in a tubular fixed bed reactor. It was activated by raising the temperature of the catalyst by 50° C./hour from ambient to 275° C. under 1 atm of a 1:1 molar ratio $H_2/CO$ blend flowing at 1160 $h^{-1}$ followed by increasing the pressure to 300 psig by 50 psi/hour. At 275° C. and 300 psi the CO conversion was 31.8%, the product contained 33.6 wt % hydrocarbons in the diesel range, and the $CO/H_2$ usage ratio was 0.96. At 700 psi at 281° C. the CO conversion increased to 40.6% (see Table 3).

EXAMPLE 8

The same catalyst used in Example 7 was activated by reducing in $H_2$ at 450° C. for 2 hours and used for CO hydrogenation at 270° C. and 300 psig in a tubular fixed bed reactor. Results of CO hydrogenation are in Table 3.

EXAMPLE 9

The same catalyst used in Example 7 was activated by reducing in $H_2$ followed by carbiding in CO for 2 hours at 250° C. It was used for CO hydrogenation at 264° C. and 300 psig in a tubular fixed bed reactor. The results are shown in Table 3.

EXAMPLE 10

The potassium promoted, calcined oxalate catalyst of Example 2 was activated by heating in He at 500° C. for 2 hours. Results of CO hydrogenation in gas phase testing are in Table 3.

EXAMPLE 11

The calcined, ferric nitrate impregnated catalyst of Example 1 was first ground to <325 mesh and then loaded into a tubular reactor. Under 1:1 molar ratio $CO/H_2$ at 1 atm pressure and GHSV (Gas Hourly Space Velocity)=277 $h^{-1}$, the catalyst was heated from ambient to 275° C. over a period of 5 hours, raising the temperature at 50° C./hour. At 275° C., the pressure was then increased at 50 psi/hour to 300 psig over a further 6 hour period. After cooling under $N_2$, the catalyst was unloaded in a $N_2$ purge box and slurried in deoxygenated paraffin oil (a commercial product of Fisher Scientific), before being transferred to a 300 ml continuous stirred tank reactor (CSTR) under $N_2$. The final loading of the reactor was 160 mls of 19.4 wt % slurry, containing 29.31 g of reduced catalyst. The CO hydrogenation activity was determined with stirring at 1200 RPM, over 300 hours of testing.

Results of testing are shown in Table 4. The activity in the liquid phase was lower than in the gas phase, but the $CO/H_2$ usage ratio increased to 2.00. The $C_9-C_{25}$ (diesel range) product was 66% at the beginning of the run.

The following examples illustrate the utility of $Fe_2O_3.ZrO_2.TiO_2$ for the production of diesel range hydrocarbons from synthesis gas. Results are given in Tables 5 and 6.

EXAMPLE 12

The catalyst in Example 5 was activated as in Example 7. Results of CO hydrogenation are shown in Table 5. The hydrocarbon distribution favored hydrocarbons in the $C_9-C_{25}$ range; the $C_{26}+$ yield was only 1.74%.

EXAMPLE 13

The catalyst in Example 5 was activated by reduction in 1 atm $H_2$ at 294 $h^{-1}$ at 450° C. for 5.5 hours. The activated catalyst was then slurried in paraffin oil in the absence of air to produce 160 ml of a 13.0 wt % suspension. Results of CO hydrogenation in a 300 cc CSTR autoclave operating at 1200 RPM are shown in Table 6.

TABLE 1

Fe/$ZrO_2$.$TiO_2$ Catalysts (impregnated)

| Example | Fe Source | Calcination | Fe | Zr | Ti | K |
|---|---|---|---|---|---|---|
| 1 | Nitrate | 510° C. - 2h | 14.70 | 34.88 | 17.51 | — |
| 2 | Oxalate | 550° C. - 2.5h | 5.46 | 19.82 | 34.30 | 0.2 |

Composition (wt %)

TABLE 2

$Fe_2O_3$/$ZrO_2$/$TiO_2$ Catalysts (co-precipitated)

| Example | Calcination | Fe | Zr | Ti | K |
|---|---|---|---|---|---|
| 3 | — | 17.84 | 22.56 | 21.78 | 0.29 |
| 4 | 550° C. - 2h | 18.23 | 19.14 | 21.88 | 7.98 |
| 5 | 500° C. - 2h | 8.45 | 29.90 | 16.37 | 0.20 |
| 6 | 500° C. - 2h | 9.93 | 27.88 | 17.71 | 9.38 |

TABLE 3

Fe/$ZrO_2$.$TiO_2$ Tubular Fixed Bed Testing

| Example | Activation | Temp °C. | Activity mole CO/ kg·h | CO Conversion % | $C_1$ | $C_5-C_{11}$ | $C_9-C_{25}$ | $C_{26}+$ | $CO/H_2$ Usage Ratio |
|---|---|---|---|---|---|---|---|---|---|
| 7 | $H_2$/CO to 275° C. | 275 | 7.89 | 31.8 | 8.39 | 27.63 | 33.60 | 7.14 | 0.956 |
| 7* | $H_2$/CO to 275° C. | 281 | 10.36 | 40.6 | 9.71 | 29.66 | 28.03 | 4.14 | 0.649 |
| 8 | $H_2$ - 450° C. | 270 | 10.28 | 18.4 | 15.07 | 36.63 | 13.08 | 0 | 0.754 |
| 9 | $H_2$ - 450° C. CO - 250° C. | 264 | 6.60 | 26.9 | 10.55 | 27.93 | 38.08 | 2.98 | 0.954 |
| 10 | He - 500° C. | 287 | 6.58 | 22.0 | 6.33 | 43.37 | 35.34 | 0 | 0.564 |

*700 psi
Conditions: GHSV = 1000, pressure = 300 psig, $H_2$/CO = 1

TABLE 4

Fe/$ZrO_2$.$TiO_2$ Slurry Phase Testing - Example 11

| Time h | P psig | T °C. | GHSV $h^{-1}$ | CO Conversion % | $H_2$ Conversion % | $CO/H_2$ Feed Ratio | Activity mol CO/ kg cat/h | $C_1$ | $C_5-C_{11}$ | $C_9-C_{25}$ | $C_{26}+$ | $CO/H_2$ Usage Ratio |
|---|---|---|---|---|---|---|---|---|---|---|---|---|
| 165.9 | 497 | 280.9 | 289.8 | 9.2 | 5.8 | 1.01 | 3.29 | 17.6 | 2.2 | 65.6 | 4.9 | 1.61 |

Selectivity wt %

TABLE 4-continued

Fe/ZrO$_2$.TiO$_2$ Slurry Phase Testing - Example 11

| Time h | P psig | T °C. | GHSV h$^{-1}$ | CO Conversion % | H$_2$ Conversion % | CO/H$_2$ Feed Ratio | Activity mol CO/ kg cat/h | Selectivity wt % | | | | CO/H$_2$ Usage Ratio |
|---|---|---|---|---|---|---|---|---|---|---|---|---|
| | | | | | | | | C$_1$ | C$_5$-C$_{11}$ | C$_9$-C$_{25}$ | C$_{26}$+ | |
| 190.4 | 680 | 280.1 | 282.9 | 8.4 | 4.1 | 0.96 | 2.86 | 26.1 | 0.2 | 58.4 | 0.5 | 2.00 |
| 238.9 | 710 | 312.1 | 281.1 | 9.5 | 4.5 | 0.95 | 3.15 | 35.6 | 6.4 | 18.8 | 4.1 | 2.00 |
| 335.0 | 711 | 312.1 | 281.4 | 8.2 | 5.8 | 0.94 | 3.39 | 34.5 | 2.5 | 17.8 | 3.6 | 1.67 |
| 394.1 | 710 | 331.5 | 281.8 | 10.9 | 9.0 | 0.95 | 3.66 | 41.4 | 5.6 | 12.5 | 1.7 | 1.16 |
| 419.6 | 719 | 331.7 | 282.0 | 12.2 | 7.2 | 0.95 | 4.10 | 46.7 | 5.0 | 6.5 | 0.2 | 1.61 |
| 514.6 | 713 | 329.6 | 132.6 | 13.2 | 15.5 | 0.89 | 2.01 | 37.5 | 5.6 | 27.5 | 1.6 | 0.76 |
| 538.6 | 714 | 329.3 | 139.3 | 18.7 | 11.7 | 1.92 | 4.16 | 36.0 | 7.0 | 21.1 | 1.4 | 3.03 |
| 562.6 | 313 | 279.6 | 343.4 | 3.6 | 3.9 | 0.97 | 1.48 | 33.0 | 7.8 | 41.0 | 0.0 | 0.90 |

TABLE 5

Fe$_2$O$_3$.ZrO$_2$.TiO$_2$ Gas Phase Testing - Example 12

| Temp °C. | HGSV h$^{-1}$ | CO Conv % | H$_2$ Conv % | Activity mole CO/kg · h | Hydrocarbon Distribution | | | | CO/H$_2$ Usage Ratio |
|---|---|---|---|---|---|---|---|---|---|
| | | | | | C$_1$ | C$_5$-C$_{11}$ | C$_9$-C$_{25}$ | C$_{26}$+ | |
| 258 | 1205 | 25.3 | 37.8 | 5.35 | 12.90 | 28.82 | 27.36 | 0 | 0.67 |
| 257 | 554 | 40.8 | 32.6 | 3.64 | 5.37 | 18.80 | 58.35 | 1.74 | 1.06 |

Condition: pressure = 300 psig, H$_2$/CO = 1

TABLE 6

Fe$_2$O$_3$.ZrO$_2$.TiO$_2$ Slurry Phase Testing - Example 13

| Time h | P psig | T °C. | GHSV h$^{-1}$ | CO Conversion % | H$_2$ Conversion % | CO/H$_2$ Feed Ratio | Activity mol CO/ kg cat/h | Selectivity wt % | | | | CO/H$_2$ Usage Ratio |
|---|---|---|---|---|---|---|---|---|---|---|---|---|
| | | | | | | | | C$_1$ | C$_5$-C$_{11}$ | C$_9$-C$_{25}$ | C$_{26}$+ | |
| 96.8 | 302 | 260.8 | 322.1 | 1.5 | 6.0 | 1.08 | 0.94 | 16.7 | 19.5 | 37.4 | 3.2 | 0.26 |
| 120.3 | 498 | 281.7 | 314.5 | 2.9 | 6.1 | 1.04 | 1.79 | 15.9 | 26.0 | 32.2 | 1.7 | 0.49 |
| 143.9 | 498 | 309.6 | 314.0 | 8.3 | 14.2 | 1.03 | 5.15 | 19.8 | 29.5 | 12.4 | 0.0 | 0.60 |
| 167.6 | 498 | 309.6 | 318.6 | 5.6 | 9.7 | 2.07 | 4.68 | 15.8 | 33.3 | 12.0 | 0.2 | 1.19 |
| 240.3 | 502 | 312.2 | 320.0 | 9.2 | 9.7 | 1.55 | 7.01 | 16.2 | 21.6 | 30.5 | 0.6 | 1.48 |
| 263.4 | 698 | 344.0 | 343.1 | 19.8 | 28.2 | 1.47 | 15.74 | 21.9 | 24.1 | 13.9 | 0.1 | 1.03 |
| 287.8 | 708 | 340.2 | 267.4 | 15.4 | 21.8 | 1.77 | 10.24 | 22.1 | 23.6 | 12.2 | 0.0 | 1.25 |
| 312.0 | 708 | 343.6 | 311.7 | 13.5 | 19.1 | 0.987 | 8.15 | 36.7 | 14.6 | 9.4 | 0.0 | 0.70 |

While this invention has been described with respect to specific embodiments thereof, it is not limited thereto. It is intended therefore that the appended claims be construed to encompass not only those forms and embodiments of the invention described above, but to such other forms and embodiments as may be devised by those skilled in the art without departure from the true spirit and scope of the invention.

INDUSTRIAL UTILITY

The industrial utility of this invention is in the conversion of carbon monoxide, together with hydrogen, to liquid hydrocarbon fuels. This utility may be particularly important in the conversion of synthesis gas, such as that produced in coal gasification processes, thereby to effect conversion of the coal gasification product into liquid hydrocarbon fuels.

We claim:

1. In a process for selective hydrogenation of carbon monoxide to C$_9$-C$_{25}$ hydrocarbons in a Fischer-Tropsch reaction, said method comprising activating a Fischer-Tropsch catalyst, and reacting carbon monoxide with hydrogen at elevated temperature and pressure in the presence of said activated catalyst, the improvement comprising of the utilization in said method of a catalyst comporising porous, solid particles, said particles containing a mixture of zirconium and titanium dioxides, said particles further containing, at least on the surfaces thereof, iron or iron oxide, and said particles still further containing up to 10%, by weight, of an alkali metal compound.

2. The process of claim 1 wherein said catalyst further comprises 5-15%, by weight iron with an atomic ratio of zirconium to titanium on the order of 1:1.

3. The process of claim 1 wherein said catalyst has a surface area of at least 100 square meters per gram.

4. In a process for selective hydrogenation of carbon monoxide to C$_9$-C$_{25}$ hydrocarbons in a Fischer-Tropsch reaction, said method comprising activating a Fischer-Tropsch catalyst, and reacting carbon monoxide with hydrogen at elevated temperature and pressure in the presence of said activated catalyst, the improvement comprising of the utilization in said method of a catalyst comprising porous, solid particles, said particles containing a mixture of zirconium and titanium dioxides, said particles further containing, interdispersed with said zirconium and titanium oxides, iron or iron oxide, and said particles still further containing up to 10%, by weight, of an alkali metal compound.

5. The process of claim 4 wherein said catalyst further comprises 5-15%, by weight iron with an atomic ratio of zirconium to titanium on the order of 1:1.

6. The process of claim 4 wherein said catalyst has a surface area of at least 100 square meters per gram.

* * * * *